United States Patent [19]
Chen

[11] Patent Number: 5,582,594
[45] Date of Patent: Dec. 10, 1996

[54] HYPODERMIC SYRINGE WITH A SAFE NEEDLE CAP

[76] Inventor: Long H. Chen, 5F, No. 91-3, Chung-Cheng Rd., Sec. 1, Taipei, Taiwan

[21] Appl. No.: 574,038

[22] Filed: Dec. 18, 1995

[51] Int. Cl.⁶ .................................................. A61M 5/00
[52] U.S. Cl. .......................... 604/110; 604/192; 604/263
[58] Field of Search ...................... 604/110, 187, 604/192, 263, 196, 197, 194, 195; 206/363–368

[56] References Cited

U.S. PATENT DOCUMENTS 4,710,170  12/1987  Haber et al. ............................ 604/110
5,041,099  8/1991  Gelabert .................................. 604/192
5,346,475  9/1994  Gregorio ................................. 604/110
5,360,423  11/1994  McCormick ......................... 604/263 X

*Primary Examiner*—John D. Yasko
*Attorney, Agent, or Firm*—Bacon & Thomas

[57] ABSTRACT

A hypodermic syringe wherein the neck of the barrel has a toothed portion raised around an inside wall thereof for passing the needle cannula and sloping in one direction; the needle cap has a plurality of toothed portions spaced around the periphery at different elevations and respectively sloping in one direction; the toothed portions of the needle cap are forced into engagement with the toothed portion of the neck of the barrel and stopped by it from backward movement when the needle cap is invertedly inserted into the neck of the barrel to seal the used needle cannula inside the barrel.

3 Claims, 5 Drawing Sheets

HYPODERMIC SYRINGE WITH A SAFE NEEDLE CAP

BACKGROUND OF THE INVENTION

The present invention relates to hypodermic syringes, and relates more particularly to such a hypodermic syringe which has a safe needle cap that can be securely fastened to the neck of the barrel in the inverted position to stop the needle cannula inside the barrel after the use of the hypodermic syringe.

The needle cannula of a hypodermic syringe must be damaged after its use, and then properly disposed of. Various safety hypodermic syringes have been disclosed, and have appeared on the market. Exemplars are seen in Taiwan Utility Patent No. 84,837, U.S. Pat. No. 5,328,475. These hypodermic syringes permit the needle cannula to be pulled backwards to the inside of the barrel after its use. However, these hypodermic syringes cannot prevent the deformed needle cannula from projecting or escaping out of the neck of the barrel because the needle cap cannot be securely fixed to the barrel to seal the neck thereof. FIG. 1 shows the needle cap of a conventional hypodermic syringe. This structure of needle cap has a plurality of longitudinal grooves around the periphery. Because the needle cap is longitudinally grooved, it can be positively seized in the hand, then disconnected from the neck of the barrel and removed from the needle cannula. However, if the needle cap is invertedly inserted into the neck of the barrel after the needle cannula has been pulled back to the inside of the barrel, it will disconnect from the neck of the barrel easily when the barrel is shaken. Therefore, this structure of needle cap cannot seal the needle cannula of the used hypodermic syringe inside the barrel.

SUMMARY OF THE INVENTION

The present invention has been accomplished to provide a hypodermic syringe with a safe needle cap which eliminates the aforesaid problem. It is one object of the present invention to provide a safe needle cap for a hypodermic syringe which can be fixedly secured to the neck of the barrel to seal the needle cannula inside the barrel after the use of the hypodermic syringe. It is another object of the present invention to provide a safe needle cap for a hypodermic syringe which can be fixedly secured to the neck of the barrel to seal the needle cannula inside the barrel after the use of the hypodermic syringe, and simultaneously to reinforce the neck of the barrel against compression force. It is still another object of the present invention to provide a safe needle cap for a hypodermic syringe which can be fixedly secured to the barrel after the use of the hypodermic syringe for easy disposal. According to the preferred embodiment of the present invention, the neck of the barrel has a toothed portion raised around an inside wall thereof for passing the needle cannula and sloping in one direction; the needle cap has a plurality of toothed portions spaced around the periphery at different elevations and respectively sloping in one direction; the toothed portions of the needle cap are forced into engagement with the toothed portion of the neck of the barrel and stopped by it from backward movement when the needle cap is invertedly inserted into the neck of the barrel to seal the used needle cannula inside the barrel.

DETAILED DESCRIPTION OF THE PREFERRED EMBODIMENT

Figure 1:
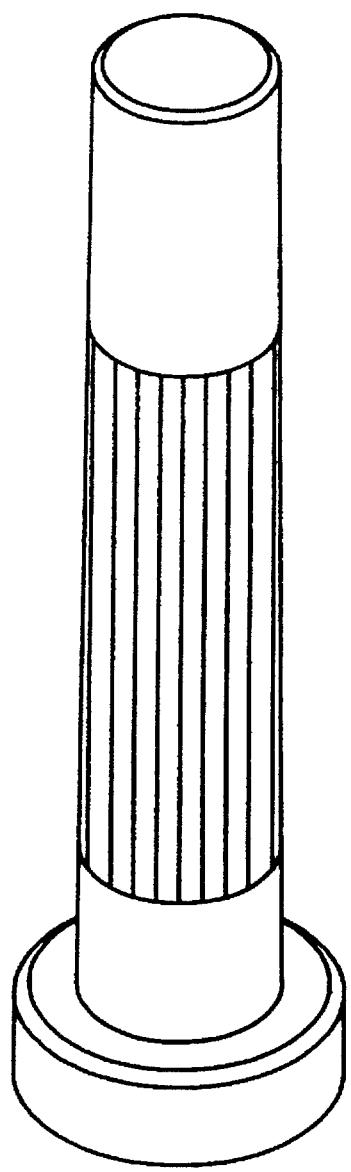
FIG. 1 is an elevational view of a needle cap according to the prior art.
Figure 2:
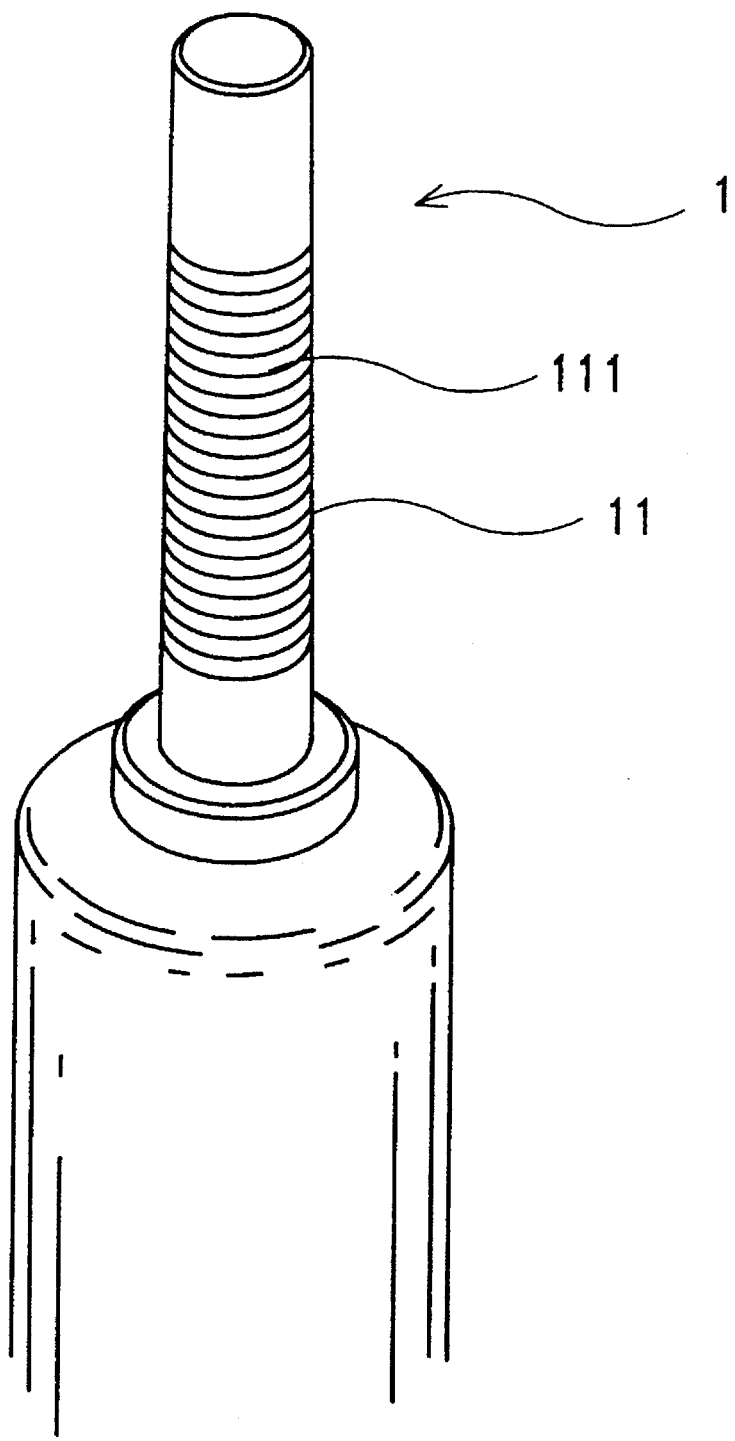
FIG. 2 shows a needle cap fastened to the neck of a hypodermic syringe and covered on the needle cannula according to the present invention.
Figure 3:
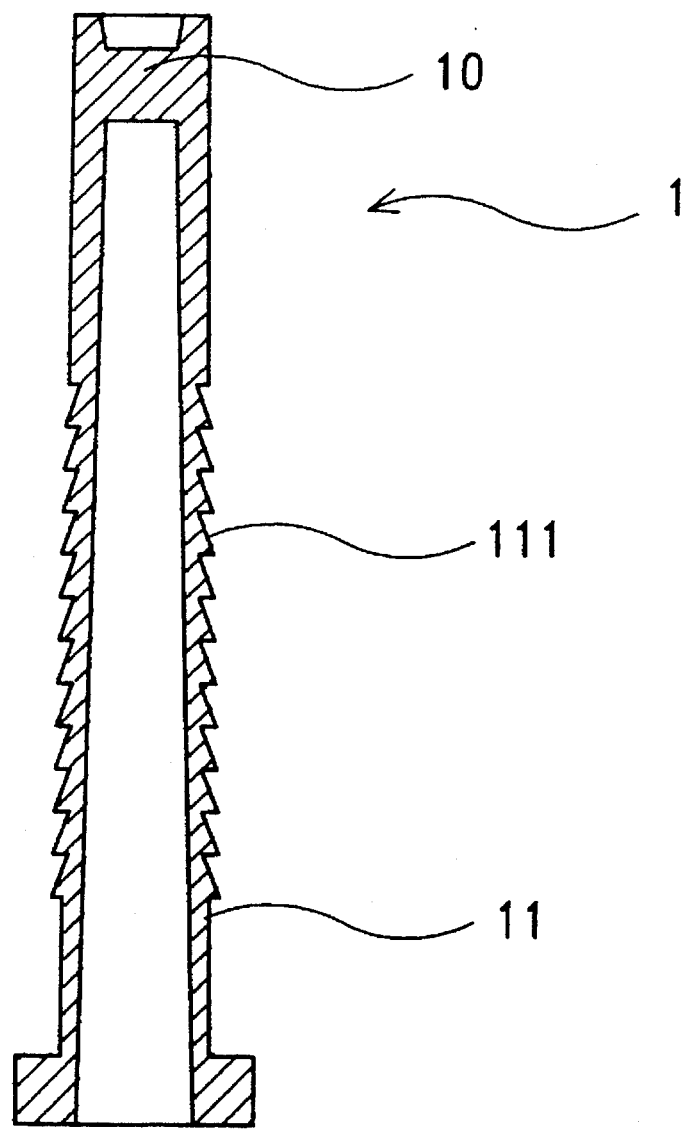
FIG. 3 is a longitudinal view in section of the needle cap shown in FIG. 2.

Referring to FIGS. 2 and 3, the needle cap, referenced by 1, has a plurality of toothed portions 111 raised around the middle part of the outside wall 11 thereof at different elevations and respectively disposed in a parallel relation. The closed cap head 10 has a certain thickness which prohibits the needle cannula from piercing through. The toothed portions 111 slope in one direction so that the needle cap 1 can be conveniently inserted into the neck of the barrel of the hypodermic syringe.

Figure 4:
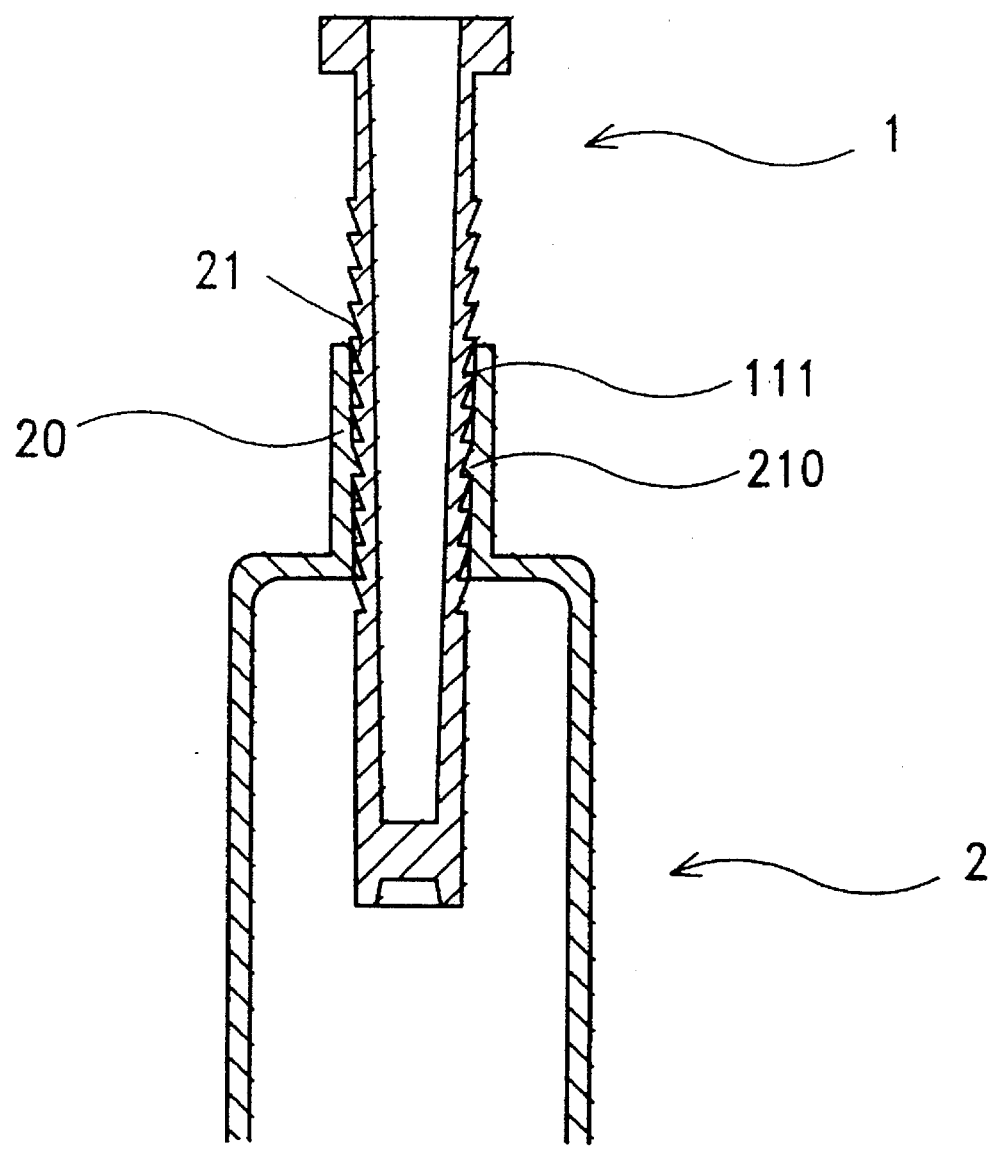
FIG. 4 is a sectional view showing the needle cap invertedly fastened to the neck of the barrel of the hypodermic syringe according to the present invention.

Referring to FIG. 4, the barrel, referenced by 2, has a neck 20 for mounting the needle cannula. The neck 20 has a toothed portion 210 raised around the inside wall 21. The toothed portion 210 slopes in one direction. The toothed portion 210 of the neck 20 permits the needle cap 1 to be inserted into the neck 20. When the needle cap 1 is inserted into the neck 20, the toothed portions 111 of the needle cap 1 are forced into engagement with the toothed portion 210 of the neck 20, and the toothed portion 210 of the neck 20 prohibits the toothed portion 111 of the needle cap 1 from backward movement, and therefore the needle cap 1 is securely fixed to the neck 20 of the barrel 2.

Figure 5:
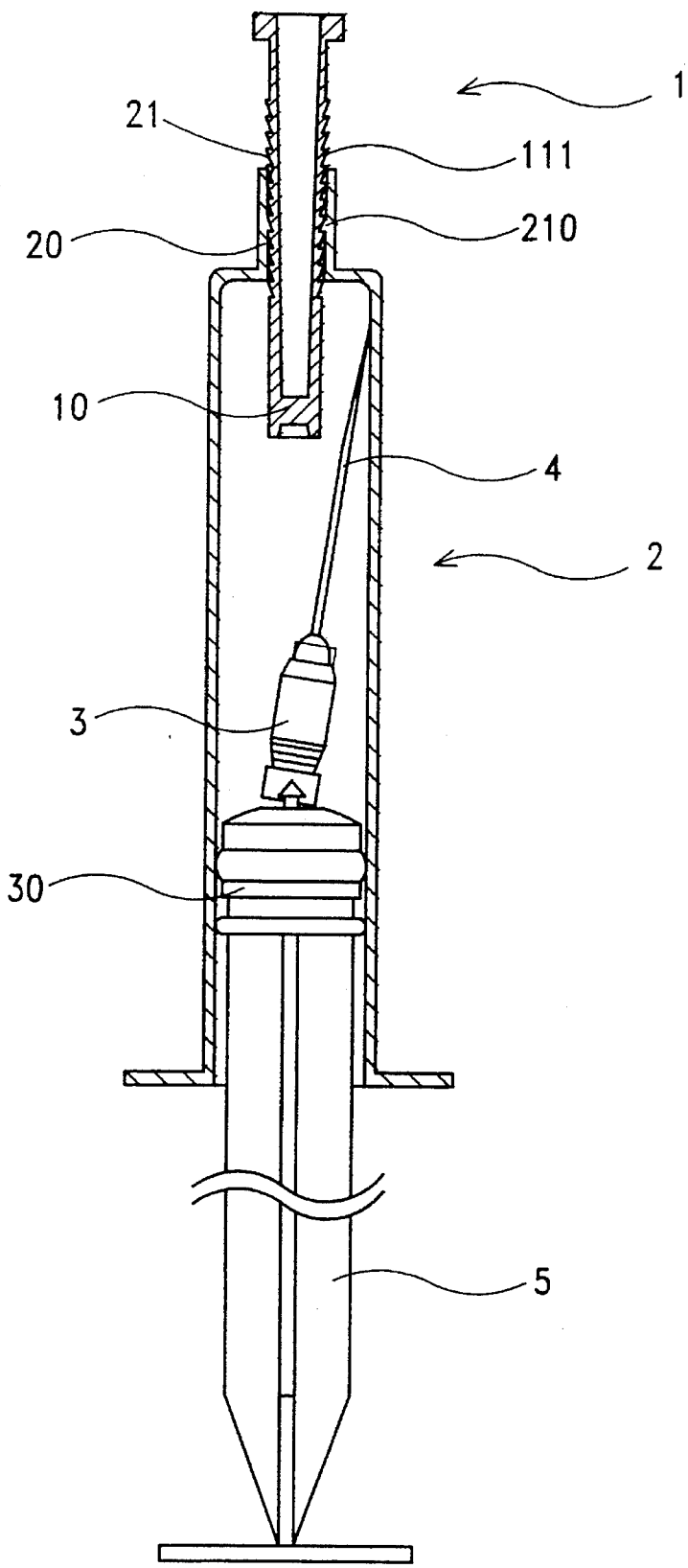
FIG. 5 is a longitudinal view in section of the hypodermic syringe according to the present invention, showing the needle cannula pulled back to the inside of the barrel, and the needle cap invertedly fastened to the neck of the barrel of the hypodermic syringe to seal the gap of the neck.

Referring to FIG. 5, after the use of the disposable hypodermic syringe, the stopper 30 is pulled backwards by the plunger 5. Because the needle cannula 4 has a connector 3 at the back, which is secured to the stopper 30 when the stopper 30 is moved to the end, the needle cannula 4 will be carried backwards to the inside of the barrel 2 by the stopper 30 when the stopper 30 is pulled backwards by the plunger 5. When the needle cannula 4 is moved to the inside of the barrel 2, the needle cap 1 is inserted into the neck 20 of the barrel 2 to force the toothed portion 111 thereof into engagement with the toothed portions 210 of the neck 20 of the barrel 2, and therefore the needle cannula 4 is sealed on the inside of the barrel 2.

I claim:

1. A hypodermic syringe of the type comprising a barrel having a neck, a needle cannula detachably fastened to the neck of said barrel, and a needle cap detachably covered on said needle cannula, wherein the neck of said barrel has a toothed portion raised around an inside wall thereof for passing said needle cannula and sloping in one direction; said needle cap has a plurality of toothed portions spaced around the periphery of said needle cap at different elevations and respectively sloping in one direction, the toothed portions of said needle cap being forced into engagement with the toothed portion of the neck of said barrel and stopped by it from backward movement when said needle cap is invertedly inserted into the neck of said barrel.

2. The hypodermic syringe of claim 1 wherein said needle cap has a closed head of a predetermined thickness which prohibits said needle cannula from piercing through.

3. The hypodermic syringe of claim 1 wherein the outer diameter of said needle cap fits the inner diameter of the neck of said barrel.

* * * * *